United States Patent [19]
Edelschick

[11] Patent Number: 4,747,818
[45] Date of Patent: May 31, 1988

[54] STABILIZING DISTURBED ARTERIAL BLOOD FLOW BY ALTERATION OF INFLOW ADMITTANCE

[76] Inventor: Donald Edelschick, 9 Trap Rock Cir., New City, N.Y. 10956

[21] Appl. No.: 5,341

[22] Filed: Jan. 13, 1987

Related U.S. Application Data

[63] Continuation of Ser. No. 640,934, Aug. 15, 1984, abandoned.

[51] Int. Cl.$^4$ ............................................. A61M 5/00
[52] U.S. Cl. ........................................................ 604/8
[58] Field of Search ........................... 604/7, 8, 49–53, 604/104, 284; 128/1 R, 334, 335

[56] References Cited
U.S. PATENT DOCUMENTS 3,316,557  5/1967  Liebig ...................................... 3/1.4
4,503,568  3/1985  Madras .................................... 3/1.4

OTHER PUBLICATIONS
Vitallium Surgical Appliances, Mar. 1948, p. 22.

Primary Examiner—John D. Yasko
Attorney, Agent, or Firm—Brooks Haidt Haffner & Delahunty

[57] ABSTRACT

Stabilizing arterial blood flow in the presence of arterial irregularities by insertion of a flow modulating device in the opening of a deformed artery to alter the admittance phasor to match the input impedance of the artery. The device comprises a plug having a central passageway therethrough adapted to receive an insert and the insert having an interior passageway therethrough which when the insert is positioned in the central passageway alters the admittance phasor to match the input impedance. This result obtains because the device reduces the interior diameter of the artery at the opening of the artery into a second, larger artery through which blood flows into the first artery from the second artery.

6 Claims, 1 Drawing Sheet

STABILIZING DISTURBED ARTERIAL BLOOD FLOW BY ALTERATION OF INFLOW ADMITTANCE

This application is a continuation, of application Ser. No. 06/640,934, filed Aug. 15, 1984, now abandoned.

This invention relates to treatment of vascular disorders associated with disturbed blood flow, and in particular provides a method and apparatus for modulating flow rate and pressure in arteries affected by disturbed blood flow so as to reduce or avert development of high shear flow and turbulent shear flow through the circulation which conditions are thought to be contributory to the pathogenesis of atherosclerosis, and arterial ischemia and occlusion.

The pressure-flow characteristics of human pulsatile arterial blood flow in branch circuits off the aorta is importantly affected by the characteristic values of the admittance of the pulse and of the input impedance of the receiving circuit to which it is applied.

Normally, the acceleration rate of arterial blood is uniform and laminar, as in stable flow through the aorta and branching arteries. The presence of arterial wall irregularity, i.e., stenosis, as in arterial walls deformed by atherosclerosis, disturbs flow by causing acceleration of blood flowing through the diseased artery, often reaching critical velocities (with associated high Reynold's Number). Such disturbed flow is associated with pathologic amounts of shear in both the narrowed arterial segment and in upstream segments as well. In the latter case turbulent shear manifests from jet flow separation, formation of vortices and flow reversal.

It is believed the power consequently lost in transmission of blood through the diseased artery (ultimately transformed into heat) denatures the artery, promoting atherosclerosis and thrombosis. It is therefore a principal object of this invention to modulate arterial flow through stenotic and otherwise deformed arteries to maximize power transmission and minimize power lost to high shear flow and turbulent shear flow, conditions which are ultimately damaging to the circulation.

Stabilization of disturbed flow is accomplished in accordance with this invention by revising the entrance orifice geometry of the artery with percutaneous insertion of a flow modulating device in the form of an arterial plug that provides a more suitable entrance geometry and passageway to the diseased artery altering the pressure-flow wave admittance phasor, so that it is beneficially matched to the input impedance of the diseased artery (such that the product of admittance times the input impedance phasor approaches unity).

For a more complete understanding of the practical application of this invention reference is made to the appended drawings in which.

Figure 1:
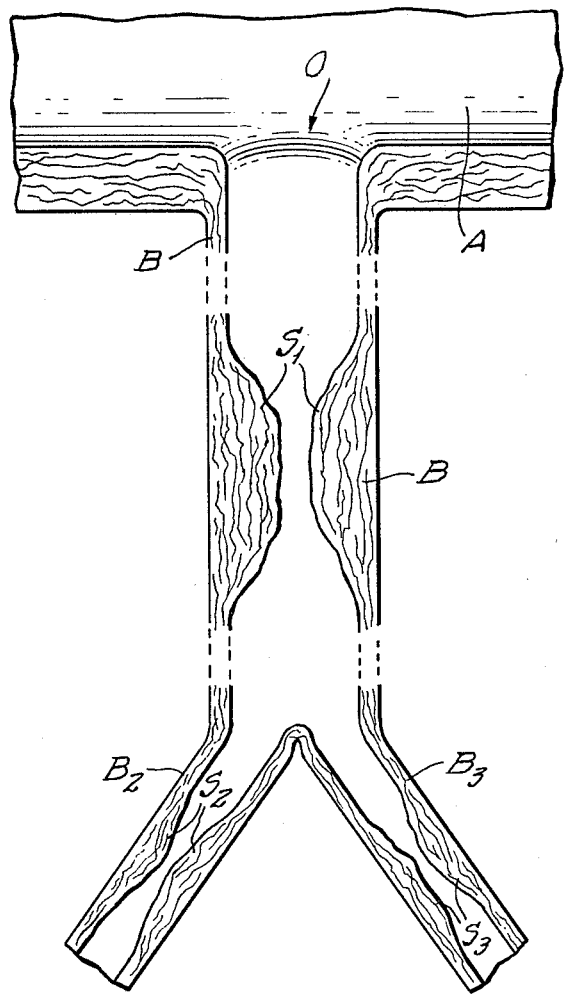
FIG. 1 is a fragmentary, sectional view of a branching artery leading from the aorta and containing stenoses in the form of plaque formations in sections of the artery.

In the drawings, specifically with reference to FIG. 1, the reference letter A represents a section of the human aorta. The section of aorta A shown in FIG. 1 includes a section through a branching artery, such as the coronary artery B, having an opening O from the interior of aorta A, and being bifurcated into branches $B_2$ and $B_3$. Coronary artery B at a location remote from aorta A has stenoses $S_1$ above the bifurcation and $S_2$ and $S_3$ in branches $B_2$ and $B_3$, respectively, in the form of atherosclerotic plaque formations constricting the lumen of artery B and of branches $B_2$ and $B_3$ having smaller cross-sections than in the adjacent sections of artery B. As a consequence of the presence of stenoses $S_1$, $S_2$ and $S_3$, blood flow proceeding from aorta A through opening O into artery B is impeded at the vicinities of stenoses $S_1$, $S_2$ and $S_3$ resulting in departure from the normal laminar flow and in a disturbed turbulent state in the vicinity of each stenosis $S_1$, $S_2$ and $S_3$.

In accordance with this invention blood pressure and flow through artery B are modulated by percutaneous insertion of a plug 10 in opening O. Plug 10 in the illustrated case is composed of two assembled parts which are shown apart in FIG. 3. Specifically, plug 10 comprises a flanged plug body 20 and a tubular insert 40.

Plug body 20 has an elongated tubular section 21 which is internally provided with a central bore 22. One end of plug body carries an annular lip 23 surrounding the opening of bore 22 at that end of plug body 20. The under side of lip 23, as seen in the drawings, that is, the side of lip 23 facing the length of tube 21 is dentate, i.e., a series of conical projections 24 are distributed about the under side of lip 23 while the opposite side of lip 23 is generally flat.

Figure 4:
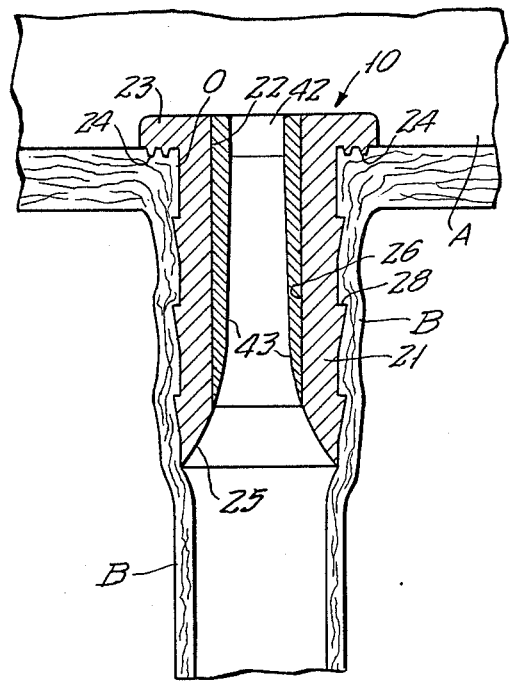
FIG. 4 is a view similar to FIG. 1 showing the assembled plug device inserted in the opening of the branch artery from the aorta.
Figure 3:
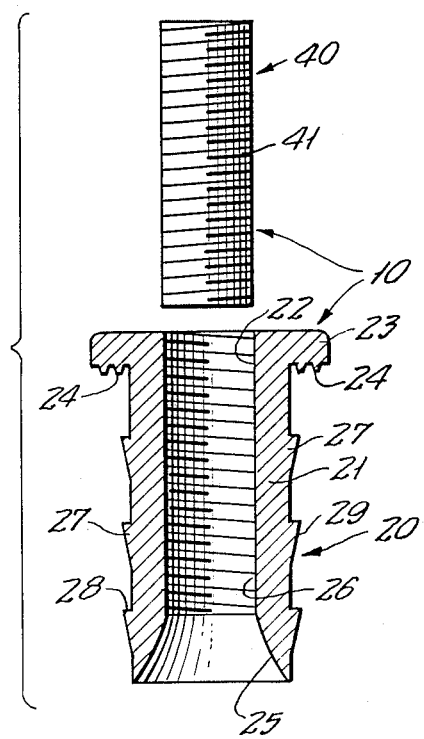
FIG. 3 is a cross-sectional exploded view of the plug device shown in FIG. 2.

The end 25 of bore 22 remote from lip flange 23 is tapered outwardly in a bell-shape, as can be seen specifically referring to FIGS. 3 and 4, while the remainder 26 of the passageway formed by bore 22 is of uniform diameter and is tapped throughout its length.

Figure 2:
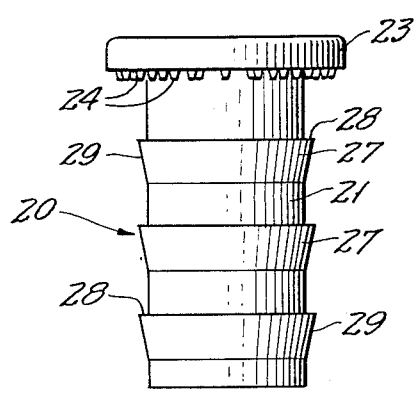
FIG. 2 is an elevation of a plug device in accordance with this invention.

Exteriorally, tube part 21 of plug body 20 is provided with annular ribs 27. Specifically, each rib 27 has an upper, abrupt shoulder 28 and is tapered downwardly and inwardly, as indicated by the reference numeral 29, toward the lower end of plug body 20, as seen best in FIG. 2. It will be apparent that the shape of ribs 27 facilitates insertion of tube 21 into a snugly fitting lumen, such as artery B, but impedes withdrawal of tube 21 from such lumen.

Insert 40 is a tube having a length equal to that of tapped passageway 26 in plug body 20. Specifically, the exterior of insert 40 is sized to fit into passageway 26 and is threaded, as indicated by the reference numeral 41, such that it can be inserted into passageway 26 by threading to a position shown in FIG. 4, fully received in tube body 20 with the upper end of insert 40 flush with the upper surface of flange 23. As seen in FIG. 4 the interior passageway 42 through insert 40 is tapered outwardly toward the lower end, as indicated by the reference numeral 43, to blend into the internally tapered, lower end 25 of tube 21.

Plug 10 parts 20, and 40 are preferably made of stainless steel or other material having strong structural properties which is inert to body fluids. Generally, metallic materials are preferred because they can be seen by radiology. If non-metallic materials are used for construction of the various parts of plug 10, they preferably should include X-ray opacifiers.

The sizes of the various parts of plug 10 will vary, dependent upon the intended site of insertion. A plug 10 intended for insertion in the opening O of a human coronary artery B typically can have an O.D. of tube body 20 on the order of 6 or 7 mm. to fit snugly into artery B. The length of tube body 21 can be on the order of 1 cm to 1.5 cm. to fit the same coronary artery, allowing for an aorta wall thickness of about 3 or 4 mm. Lip 23 typically, in this context, can have an O.D. of 10 mm. and a base thickness of 1 mm. with projections 24 adding another 0.5 mm. in thickness to lip 23. Tube 21 can have a thickness of about 1 mm. but such thickness is a matter of structional integrity and may be greater, dependent on the ultimate I.D. of insert 40.

It will be apparent that plug 10 is inserted into opening O to be received in artery B. In inserting plug 10 plug body 20 is manipulated on the end of an elongated rod or catheter device which can be percutaneously inserted through a larger artery, such as a brachial or femoral artery at a site remote from aorta A. On inserting plug body 20 into opening O, lip 23 remains inside aorta A and tube 21 extends down artery B.

As ribs 27 slide into artery B, they grip the endothelial wall of artery B firmly such that accidental withdrawal of plug body 20 from opening O is impeded. When plug body 20 is fully inserted, lip 23 presses against the wall of aorta A such that projections 24 aid in preventing rotation of plug body 20 relative to the endothelial wall of aorta A.

Needless to say, the outside diameter of tube 21 is sized to approximate the inside diameter of artery B. The inside diameter of passageway 42 through insert 40 is carefully selected and is determined by continuous measurement of the pressure and flow rates of blood through plug body 20 during cardiac cycles by minaturized pressure and flow rate meters. The input impedance of artery B can then be evaluated, and the appropriate inside diameter of passageway 42 of insert 40 at the opening thereof adjacent lip 23 to give the most beneficial admittance characteristic can be determined. It will be appreciated that fluctuations in blood pressure and heart rate which normally occur produce fluctuations in admittance and therefore result in deviations from the desired exact match to impedance phasor. Measurement should be taken under circumstances leading to the best approximation of average conditions such that the worst match allowed is still conducive to stable flow.

The appropriate sized insert 40 is then manipulated similarly to plug body 20 to position insert 40 inside tube 21 and thread it to be fully received in tube 21, as shown with reference to FIG. 4.

I claim:

1. A device for altering blood flow to be positioned at an opening between a first artery and a larger second artery through which blood flows into said first named artery from said second, larger artery, said first artery having an input impedance, said second, larger artery having an admittance phasor, and said device comprising:

a plug having a central passageway therethrough adapted to receive an insert, and said insert having an interior passageway therethrough which when said insert is positioned in said central passageway alters the admittance phasor to match the input impedance.

2. A device according to claim 1 wherein said plug further comprises a plug body having annular ribs which facilitate insertion into the first artery and impede withdrawal therefrom, and an annular lip having a dentate under side and a generally flat upper side, said annular lip at an upper end of the plug body and surrounding the central passageway whereby said lip sits within the second artery.

3. A device according to claim 2 wherein said central passageway of said plug further comprises an outwardly tapered end at a lower end of the plug body, and a portion of generally uniform diameter from said tapered end upwards to the upper end of the plug body.

4. A device according to claim 1 wherein a portion of said central passageway is tapped and said insert has a threaded outer surface which mates with the tapped central passageway.

5. A device according to claim 3 wherein the portion of generally uniform diameter of said central passageway is tapped and said insert has a threaded outer surface which mates with the tapped central passageway.

6. A device according to claim 5 wherein the interior passageway is outwardly tapered toward the lower end of the plug body.

* * * * *